United States Patent [19]
Richtler et al.

[11] Patent Number: 4,874,552
[45] Date of Patent: Oct. 17, 1989

[54] PROCESS FOR SIMULTANEOUS BLEACHING AND NEUTRALIZATION OF ALPHA-SULFOFATTY ACID ESTERS

[75] Inventors: Hans-Joachim Richtler, Moenchengladbach; Udo Kreutzer, Monheim; Franz-Josef Carduck, Haan; Klaus Koester, Langenfeld; Hubert Harth, Duesseldorf, all of Fed. Rep. of Germany

[73] Assignee: Henkel Kommanditgesellschaft auf Aktien, Duesseldorf, Fed. Rep. of Germany

[21] Appl. No.: 62,736

[22] Filed: Jun. 15, 1987

[30] Foreign Application Priority Data

Jun. 14, 1986 [DE] Fed. Rep. of Germany ....... 3620158

[51] Int. Cl.$^4$ ............................................ C07C 143/12
[52] U.S. Cl. .................................................. 260/400
[58] Field of Search ......................................... 260/400

[56] References Cited

U.S. PATENT DOCUMENTS 2,846,457  8/1958  Zemlin et al. ...................... 260/400
3,151,136  9/1964  Koczorowski et al. ............. 260/400
3,485,856  12/1969  Wulff et al. ........................ 260/400
4,547,318  10/1985  Kloetzer et al. .................... 260/400

*Primary Examiner*—Anton H. Sutto
*Attorney, Agent, or Firm*—Ernie G. Szoke; Wayne C. Jaeschke; Henry E. Millson, Jr.

[57] ABSTRACT

For the production of solid, substantially anhydrous alkali metal salts of α-sulfofatty acid alkyl esters containing from 8 to 22 carbon atoms in the fatty acid chain and from 1 to 6 carbon atoms in the ester alkyl radical, solid or molten α-sulfofatty acid alkyl esters are simltaneously mixed with an aqueous solution of hydrogen peroxide or an $H_2O_2$-yielding compound and with solid alkali metal carbonate at a temperature of from 20° to 80° C. optionally in the presence of aqueous alkali metal hydroxide, the ratio by weight of ester of $H_2O_2$ being from 1:0.01 to 1:0.06 and the molar ratio of ester to alkali metal carbonate being in the range of from 1:0.5 to 1:0.75, the foam formed through the release of $CO_2$ is mechanically destroyed under a pressure of from 0.2 to 1.0 bar and at a temperature of from 50° to 70° C., and the product formed is residually degassed and residually dehydrated under a pressure of from 15 to 50 mbar and a temperature of from 50° to 80° C.

17 Claims, No Drawings

PROCESS FOR SIMULTANEOUS BLEACHING AND NEUTRALIZATION OF ALPHA-SULFOFATTY ACID ESTERS

BACKGROUND OF THE INVENTION

1. Field of the Invention

This invention relates to a process for the production of solid alkali metal salts of α-sulfofatty acid alkyl esters containing less than 10% water, which are suitable for use as detergents in washing and cleaning preparations, by simultaneous bleaching and neutralization.

2. Statement of Related Art

The production of alkali metal salts of α-sulfofatty acid alkyl esters ("ester sulfonates") by sulfonation of fatty acid methyl esters with gaseous $SO_3$ and subsequent neutralization of the sulfonic acids formed with aqueous alkali metal hydroxides, for example with sodium hydroxide, has been known for some time, The end products of this process, i.e. the alkali metal salts of the corresponding α-sulfofatty acid alkyl esters, are predominantly used as detergents in washing and cleaning preparations.

However, all hitherto known production processes have remained unsatisfactory either because, although light colored end products suitable for direct use in the detergent industry can be obtained, the yields of the sulfonation step leading to those products are highly unsatisfactory, or because although high sulfonation yields can be obtained, the color instability of the fatty acids or fatty acid esters in the sulfonation step means that dark-colored to brown-black crude products unsuitable for direct use in washing and cleaning preparations are regularly obtained. Accordingly, a sulfonation step taken to high product yields normally has to be followed by bleaching of the dark α-sulfofatty acid derivatives formed in the sulfonation step to obtain light-colored products suitable for use in washing and cleaning systems.

Another difficulty of hitherto known process for the production of aqueous ester sulfonates is that, in the course of the production process, the products accumulate in the form of water-containing pastes having an active-substance content of up to 70%. However, pastes such as these can no longer be pumped on their own, i.e. in the absence of further additives, above ester sulfonate concentrations of from 30% to 40%. Accordingly, the viscosity behavior of ester sulfonate pastes such as these always involves the risk of blockages in apparatus and pipes. Accordingly, there has long been a need to find production processes for alkali metal salts of α-sulfofatty acid alkyl esters in which which the high viscosity of the products obtained is harmless to the process.

CA vol. 101(1984)56874j (Japanese published patent application No. 84-16870) describes a process for the production of α-sulfofatty acid ester salts, in which α-sulfofatty acid esters formed during the sulfonation step are bleached with $H_2O_2$ in the presence of a polycarboxylic acid or one of its salts and subsequently converted by neutralization into the corresponding α-sulfofatty acid esters salt. Although the salts formed are very suitable for use as detergents in washing and cleaning preparations, the reaction time required for the bleaching step is of the order of 1 hour which does not include the time required for the following neutralization reaction.

U.S. Pat. No. 4,547,318 describes a process for the production of color-stable, light-colored aqueous salt pastes of washing-active α-sulfofatty acid esters in which the dark-colored α-sulfofatty acid esters emanating from the sulfonation step are first prebleached with alkali metal hyperchlorites in neutral to mildly alkaline aqueous solution and are then fully bleached with hydrogen peroxide in the usual way in a mildly acidic aqueous solution. The bleaching process as a whole takes several hours, involves a change in the pH value of the reaction medium with all the ensuing disadvantages and gives aqueous salt pastes of which the active substance content is in the range of from 20 to 60% by weight which, as described above, gives rise to problems affecting the process due to the considerable increase in viscosity with increasing active substance content.

STATEMENT OF THE INVENTION

Other than in the operating examples, or where otherwise indicated, all numbers expressing quantities of ingredients or reaction conditions used herein are to be understood as modified in all instances by the term "about".

It has now surprisingly been found that solid α-sulfofatty acid alkyl ester salts substantially free from water and having outstanding color values and high color stability can be obtained by carrying out the bleaching and neutralization of the dark-colored α-sulfofatty acid alkyl esters resulting from the sulfonation step in one and the same process step.

Accordingly, the present invention relates to a process for the production of solid, substantially anhydrous alkali metal salts of α-sulfofatty acid alkyl esters by oxidative bleaching and neutralization of α-sulfofatty acid alkyl esters containing from 8 to 22 carbon atoms in the fatty acid chain and from 1 to 6 carbon atoms in the ester alkyl radical, in an apparatus suitable for the processing of paste-form products. The solid or molten α-sulfofatty acid alkyl esters are mixed at 20° to 80° C. simultaneously with an aqueous solution of hydrogen peroxide or an $H_2O_2$-yielding compound and with solid alkali metal carbonate, optionally in the presence of aqueous alkali metal hydroxide, the ratio by weight of ester to $H_2O_2$ being from 1:0.01 to 1:0.06 and the molar ratio of ester to alkali metal carbonate being from 1:0.5 to 1:0.75, the foam formed through the release of $CO_2$ being mechanically destroyed under a pressure of from 0.2 to 1.0 bar and at a temperature of from 50° to 70° C. The product formed is residually degassed and residually dehydrated with mechanical agitation under a pressure of from 15 to 100 mbar and at a temperature of from 50° to 80° C. and the solids formed are blended by known methods.

Any apparatus, plants or units suitable for the processing of paste-form products can be used for carrying out the process according to the invention, providing they are of such a construction that the corresponding degassing process steps may be carried out in vacuo and any foam formed can be mechanically destroyed. Suitable apparatus includes, for example, correspondingly equipped stirring autoclaves and trough-type heat exchangers. Evacuable kneaders, for example Z-kneaders, are preferably used. If, as in one preferred embodiment, the process of the invention is continuously carried out, continuous solid/liquid mixers may be used. Injection-type mixers or mixers working on the rotor-stator principle have proven to be particularly suitable for this purpose.

The α-sulfofatty acid alkyl esters used as starting materials for the process of the invention emanate from the processes typically used in the prior art for the sulfonation of fatty acid alkyl esters. Esters such as these are obtained from synthetic, semi-synthetic or natural oils and/or fats which may in turn originate from plants, land animals or aquatic animals. Their fatty acid residues contain from 8 to 22 carbon atoms and preferably from 12 to 18 carbon atoms. Accordingly, the fatty acids are lauric acid, trideconoic acid, myristic acid, pentadecanoic acid, palmitic acid, margaric acid or stearic acid. The ester group of the fatty acid alkyl esters normally contains from 1 to 6 and preferably from 1 to 3 carbon atoms, the corresponding methyl esters being particularly preferred. These esters are generally formed by saponification of synthetic, semi-synthetic or natural oils and/or fats and mixtures thereof and reaction of the fatty acids formed with monohydric alcohols containing from 1 to 6 carbon atoms or by direct transesterification with the corresponding alcohols, particularly methanol. The corresponding fatty acid esters are then sulfonated in known manner at elevated temperature with a mixture of gaseous sulfur trioxide and inert gas in a sulfonation reactor, resulting in the formation of products having a degree of sufonation of more than 90° C. which are more or less dark in color due to the color instability of the fatty acid alkyl esters.

In the process of the invention, neutral to mildly alkaline α-sulfofatty acid alkyl ester salts ("ester sulfonates") having a water content of less than 10% and Klett color values below 100 can be prepared by simultaneous oxidative bleaching and neutralization. The starting materials used are the crude products of the sulfonation of fatty acid alkyl esters containing from 8 to 22 carbon atoms and preferably from 12 to 18 carbon atoms in the fatty acid chain, i.e., α-sulfofatty acid alkyl esters.

Bleaching is carried out with hydrogen peroxide or compounds which release hydrogen peroxide in aqueous solution under the reaction conditions. The simultaneous neutralization is carried out with alkali metal carbonates, particularly sodium carbonate. In the course of this simultaneous bleaching and neutralization reaction, the bleaching effect of the hydrogen peroxide is surprisingly enhanced to a significant extent by comparison with two-step bleaching and neutralization treatments known from the prior art. There is thus no need for a second alkaline bleaching treatment. Neutral to mildly alkaline solids which may be pelletized, granulated or flaked by methods known per se are obtained as the products of the simultaneous bleaching and neutralization reaction upon cooling of the reaction mixture to room temperature the products are not tacky and are readily soluble in water.

The more or less dark-colored α-sulfofatty acid alkyl esters obtained from the sulfonation of fatty acid alkyl esters are used in substantially anhydrous form in the process of the invention. The starting materials may be solid or molten, depending on the α-sulfofatty acid alkyl esters used as raw material and the particular reaction temperature selected. The reaction temperature is normally in the range of from 20° to 80° C., a temperature range of from 50° to 80° C. being particularly preferred for carrying out the bleaching and neutralization process according to the invention. At high temperatures, for example at temperatures of from 60° to 80° C., the α-sulfofatty acid alkyl esters used are preferably present in molten form.

An aqueous solution of hydrogen peroxide or a compound yielding hydrogen peroxide and a solid alkali metal carbonate are simultaneously added in the temperature range indicted to the α-sulfofatty acid alkyl esters used as starting materials, of which—as described above—the methyl esters are particularly preferred by virtue of their ready accessibility from native sources, such as tallow, coconut oil or palm kernel oil, after reaction with methanol. Hydrogen peroxide solutions having an $H_2O_2$ content of from 30 to 70% by weight are preferably used in practice. The safety precautions required for the handling of concentrated hydrogen peroxide solutions have to be taken here. The concentration of compounds yielding hydrogen peroxide is gauged in such a way that the solutions make available a quantity of hydrogen peroxide which corresponds to the concentration range specified above for $H_2O_2$.

As set forth above, the ratio by weight of α-sulfofatty acid alkyl ester to $H_2O$ should be adjusted to a value of from 1:0.01 to 1:0.06 and the molar ratio of α-sulfofatty acid alkyl ester to alkali metal carbonate to a value of from 1:0.5 to 1:0.75. The ratio by weight of ester to $H_2O_2$ is preferably from 1:0.03 to 1:0.05 while the molar ratio of ester to alkali metal carbonate is preferably from 1:0.5 to 1:0.65.

In the process of the invention, the α-sulfofatty acid alkyl ester or the ester mixtures obtained directly from the sulfonation of native fatty acid alkyl esters, which are preferably used as starting materials by virtue of their ready accessibility, are mixed as such with the bleach and the neutralizing agent in a suitable mixer, the aqueous bleaching solution and the neutralizing agent being added in portions over a short period to avoid overfoaming of the reaction mixture. The reaction begins spontaneously. The beginning of the reaction is reflected in the foaming (under the effect of carbon dioxide released) and gradual lightening of the mixture. Depending on the type and quantity of starting material used, from 30 to 80 L $CO_2$/kg sulfonic acid used (as measured under normal conditions) are released in this reaction step.

In one preferred embodiment of the process according to the invention, part of the soda in the bleaching and neutralization mixture may be replaced by an addition of alkali metal hydroxide. In this case, a bleaching/neutralization mixture containing the above-described quantities and concentrations of hydrogen peroxide is used in which the molar ratio of ester to alkali metal carbonate is from 1:0.5 to 1:0.525 and the molar ratio of ester to alkali metal hydroxide in the range of from 1:0.03 to 1:0.08. This means that (based on the quantity of α-sulfofatty acid alkyl ester) a slight excess (100 or 105% of the stoichiometric quantity) of alkali metal carbonate and 3 to 8% of an aqueous alkali metal hydroxide solution are used. An aqueous solution of NaOH is preferably used for this purpose. This solution advantageously has a concentration of 50% NaOH.

In the process of the invention, any alkali metal carbonates can be used either individually or in admixture as the alkali metal carbonate both in the presence and in the absence of the aqueous alkali metal hydroxide solution. However, sodium carbonate is preferably used for the process of the invention by virtue of its inexpensive availability.

The mixing of the α-sulfofatty acid alkyl esters or mixtures thereof with the bleaching agent and the neutralizing agent (peroxide and alkali metal carbonate, optionally in the presence of alkali metal hydroxide) is accompanied by the formation of a fine-cell, stable foam which has to be degassed and dehydrated for the preparation of the solid, color-lightened α-sulfofatty acid alkyl ester salts. According to the invention, this is done in two steps. In the first degassing step, the α-sulfofatty acid alkylester salt foam formed through the release of $CO_2$ is mechanically destroyed under atmospheric pressure or in a slight vacuum, i.e. in a pressure range of from 0.02 to 1.0 bar. This is done in a stirring autoclave, kneader, trough-type heat exchanger with self-cleaning mixing and kneading shafts or in any similar container suitable for use as a degassing apparatus. This container is thermostatically controlled to a temperature of from 50° to 70° C. to dissipate the heat of neutralization released. The residence time of the reaction mixture in the container required for degassing in the first step is from 5 to 15 minutes. The residenced time is at the lower end of this range if, as is preferably the case, degassing is carried out under a pressure of from 0.2 to 0.5 bar. A large part (approximately 60 to 90%) of the carbon dioxide formed is actually removed from the reaction mixture during this residence time. The viscosity and density of the mixture increase as degassing progresses. The product becomes increasingly tackier.

In a second step, the reaction mixture is residually degassed and residually dehydrated in vacuo. This second step is carried out under a pressure of from 15 to 100 mbar and the corresponding degassing containers are therostatically controlled to a temperature range of from 50° to 80° C. The remaining carbon dixoide is driven out in vacuo with intensive kneading or in a mechanically produced thin layer, for example in a trough-type heat exchanger or thin layer evaporator, and a large part of the water introduced with the bleaching agent and the neutralizing agent and formed during the neutralization reaction is removed at the same time. The residence time of the reaction mixture in this residual degassing and residual dehydration step is also a matter of minutes. The products obtained as degassing progresses are wax-like or soap-like, non-fluid masses of light α-sulfofatty acid alkyl esters which, in molten form, have a viscosity of more than 1000 Pa.s and which solidify on cooling to room temperature.

The solids obtained in this way can then be blended by methods known per se. This may be done using standard screw extruders so that thin strands of α-sulfofatty acid alkyl esters are obtained as the end product. No other additives are necessary. Solid products containing more than 80% washing-active substance are obtained in this way.

All the products obtained in the process according to the invention are non-tacky and dissolve readily in water. They are thus distinguished with advantage from known α-sulfofatty acid alkyl esters containing relatively large quantities of water, of which the processing on an industrial scale involves major difficulties due to the viscosity behavior peculiar to these products.

An immediate advantage of the process of the invention is that the total reaction and degassing time from the introduction of the dark-colored fatty acid alkyl esters sulfonated in the α-position to the formation of the light colored reaction products is in the range of from 15 to 45 minutes, depending on the concentration of the reactants and the color value of the esters used, and is thus distinctly shorter than in the state-of-the-art processes, all of which involve several steps. In addition, the products formed have an extremely high solids or active-substance content and are very much easier to further process and use as detergents in washing and cleaning preparations than state-of-the-art products. Alkali metal salts of α-sulfofatty acid esters prepared from crude α-sulfofatty acid esters by neutralization and, optionally, bleaching always contain a certain proportion of dialkali metal salts of the free α-sulfofatty acids. These disalts emanate partly from the alkaline hydrolysis of the mixed anhydrides of α-sulfofatty acid esters and methyl sulfuric acid proportionately present in the crude sulfonation product. Another proportion of disalt emanates from the unwanted alkaline hydrolysis of the α-sulfofatty acid methyl ester at elevated temperature and at pH values of 9 and higher. It has surprisingly been found that the alkali metal salts of α-sulfofatty acid esters prepared by the process according to the invention do not have a higher disalt content than those prepared by known processes although solid alkali metal carbonate, optionally in combination with aqueous alkali metal hydroxide, is used here as neutralizing agent.

The improvement in the color values obtained by the process of the invention leads to light-colored solids which are suitable for use as detergents in washing and cleaning preparations without any need for further bleaching or cleaning. The Klett color values obtainable are always below 100 in the process of the invention and are thus distinctly better than in known multi-step bleaching and neutralization processes.

The invention is illustrated by not limited by the following Examples.

EXAMPLE 1

600 g fused α-sulfofatty acid methyl ester (basis: Palm kernel oil, length of the fatty acid chain: 12 to 18 carbon atoms, acid number: 232, Klett color value: 250) were melted by heating to 60° C. in a Jahnke & Kunkel Z-Kneader. 34.3 g 35% aqueous hydrogen peroxide solution and 158 g sodium carbonate were added to the ester from separate supply vessels over a period of 5 minutes and mixed therewith, the addition being controlled in such a way that overfoaming of the kneader was avoided. The kneader was thermostatically controlled to 50° C. to dissipate the heat of neutralization. The foam formed was destroyed by the mechanics of the kneader.

Ester, hydrogen peroxide and soda were kneaded for 20 minutes at atmospheric pressure, the carbon dioxide partly escaping, and the color of the mixture lightening considerably.

The foamy, tacky material was then degassed in vacuo for 30 minutes at 60° C., the pressure being continuously reduced from 1.0 bar to 25 mbar.

A paste which solidified on cooling to room temperature was formed.

Analytical data of the product:
pH value of a 1% solution: 6.9
Klett color value: 35
Water content: 1.4%
Disalt content: 22% (corresponding to the anhydride content of the ester used)
WAS-content: 89%

In this and the following Examples, the Klett color value was measured with a 5% aqueous solution of the product in a cell (layer thickness 4 cm) using a blue filter at 400 to 465 nm.

In this and the following Examples, the pH-value was measured in a 1% aqueous solution of the product using a glass electrode.

In this and the following Examples, the acid number and the disalt content were determined by potentiometric titration. The content of washing-active substance (WAS) was determined by Epton titration.

EXAMPLE 2

600 g of the α-sulfofatty acid methyl ester based on palm kernel oil described in Example 1 were processed in the same way as described in that Example except that 138.5 g sodium carbonate (corresponding to a 5% excess beyond the soichiometric quantity) and 30 g of a 50% aqueous sodium hydroxide were used in addition to the quantity of hydrogen peroxide described in Example 1.

The reaction mixture was treated in the same way as in Example 1. A solid paste having the following analytical data was obtained:
pH value of a 1% solution: 8.2
Klett color value: 39
Water content: 1.5%
Disalt content: 23%
WAS content: 84%

EXAMPLE 3

An α-sulfofatty acid methyl ester was prepared in the same way as described in Example 1, except that the starting material used was an α-sulfofatty acid methyl ester based on tallow of which the fatty acid residue contained from 16 to 18 carbon atoms (acid number: 197; Klett color value; 1000). 600 g of the α-sulfofatty acid methyl ester, 84 g 35% hydrogen perixide solution and 123 g sodium carbonate were used. The product had the following analytical data:
pH value of a 1% solution: 7.7
Klett color value: 70
Water content: 3.3%
Disalt content: 24%
WAS content: 83%

EXAMPLE 4

3 kg of an α-sulfofatty acid methyl ester (number of carbon atoms in the fatty acid chain: 12 - 18; acid number 232; Klett color value: 250) were melted in a DTB-3b-trough-type heat exchanger (manufactured by the List company, Pratteln, Switzerland), followed by the addition of 720 g of sodium carbonate and 171 g of a 35% aqueous hydrogen peroxide solution. The heavily foaming, light yellow product was degassed for 15 minutes under a pressure of 0.2 bar. For residual degassing, the pressure was reduced to 25 mbar. During the residual degassing step, the container was thermostatically controlled to 60° C. In addition to carbon dioxide, 150 ml H$_2$O were removed during the 20-minute degassing process. A yellowish-white, wax-like product was formed, solidifying into a friable mass on cooling to room temperature. This mass was extruded into thin strands in a Buss-Ko kneader.

Analytical data of the product:
pH-value of a 1% aqueous solution: 6.8
Klett color value: 40
Water content: 1.3%
Disalt content: 20.5%
WAS content: 83%

EXAMPLE 5

200 g of an α-sulfofatty acid methyl ester based on coconut oil (acid number: 232; Klett color value: 250) were bleached and neutralized for 30 mins. at 60° C. in a kneader with 112 g H$_2$O$_2$ (35% aqueous solution), 46.8 g sodium carbonate and 10 g 50% aqueous sodium hydroxide. The product was then degassed in vacuo (total reaction time: 60 mins.).

The substantially colorless reaction product had the following analytical data:
pH-value of a 1% aqueous solution: 6.9
Klett color value: 17
Disalt content: 19.5%
WAS content: 85%

EXAMPLE 6

In an injection mixer (cf. pamphlet entitled "The FMC Continuous High-Performance Injection Mixer", FMC Food Machinery Europe, 1983, printed in Belgium), 50 kg/h of a melt of α-sulfofatty acid methyl ester based on coconut oil were continuously mixed while cooling with 13.2 kg/h sodium carbonate and 4.3 kg/h of a 35% by weight aqueous H$_2$O$_2$ solution. The resulting white foam was mechanically destroyed in a paddle screw and then degassed and dehydrated in vacuo. The substantially colorless reaction product solidified below 55° C. and was ground into a powder. The analytical data were as follows:
pH value of a 1% aqueous solution: 6.9
Klett color value: 70
Water content: 2.4%
Disalt content: 22%
WAS content: 92%

We claim:

1. A process for the production of solid, substantially anhydrous alkali metal salts of α-sulfofatty acid alkyl esters by oxidative bleaching and neutralization of α-sulfofatty acid alkyl esters containing from 8 to 22 carbon atoms in the fatty acid chain and from 1 to 6 carbon atoms in the ester alkyl radical, comprising the steps of
   (a) simultaneously mixing together solid or molten α-sulfofatty acid alkyl esters, an aqueous solution of hydrogen peroxide or an H$_2$O$_2$- yielding compound, and solid alkali metal carbonate at a temperature of from about 20 to about 80° C., wherein the ratio by weight of ester to H$_2$O$_2$ is from about 1:0.01 to about 1:0.06 and the molar ratio of ester to alkali metal carbonate is in the range of from about 1:0.5 to about 1:0.75,
   (b) destroying the foam formed through the release of CO$_2$ under a pressure of from about 0.2 to about 1.0 bar, and at a temperature of from about 50° to about 70° C., and
   (c) degassing and dehydrating the product formed under a pressure of from about 15 to about 100 mbar and at a temperature of from about 50° to about 80° C.

2. The process of claim 1 wherein step (a) is carried out in a stirring vessel, a kneader, or a screw mixer.

3. The process of claim 1 wherein molten α-sulfofatty acid alkyl esters are used in step (a).

4. The process of claim 1 wherein α-sulfofatty acid alkyl esters containing from 12 to 18 carbon atoms in the fatty acid chain are used in step (a).

5. The process of claim 1 wherein the α-sulfofatty acid alkyl esters contain from 1 to 3 carbon atoms in the alkyl ester radical.

6. The process of claim 4 wherein the α-sulfofatty acid alkyl esters contain from 1 to 3 carbon atoms in the alkyl ester radical.

7. The process of claim 1 wherein the α-sulfofatty acid alkyl ester is a methyl ester.

8. The process of claim 1 wherein in step (b) the foam is destroyed by mechanical means.

9. The process of claim 1 wherein step (c) is carried out with mechanical agitation.

10. The process of claim 1 wherein in step (a) an about 30 to an about 70% by weight aqueous solution of hydrogen peroxide in a ratio by weight of ester to $H_2O_2$ of from about 1:0.03 to about 1:0.05 is employed.

11. The process of claim 1 wherein in step (a) an alkali metal hydroxide is present and wherein the molar ratio of ester to alkali metal carbonate is from about 1:0.5 to about 1:0.525 and the molar ratio of ester to alkali metal hydroxide is from about 1:0.03 to about 1:0.08.

12. The process of claim 1 wherein in step (a) the alkali metal carbonate is sodium carbonate.

13. The process of claim 11 wherein the alkali metal hydroxide is sodium hydroxide.

14. The process of claim 1 wherein step (a) is carried out at a temperature of from about 50° to about 80° C.

15. The process of claim 1 wherein step (b) is carried out a under a pressure of from about 0.2 to about 0.5 bar.

16. The process of claim 1 wherein in step (a) an aqueous solution of hydrogen peroxide, and sodium carbonate are employed at a temperature of from about 50° to about 80° C., and step (b) is carried out at a pressure of from about 0.2 to about 0.5 bar.

17. The process of claim 1 wherein step (a) is carried out in the presence of an aqueous alkali metal hydroxide.

* * * * *